United States Patent
Çakar et al.

(10) Patent No.: US 11,918,627 B2
(45) Date of Patent: Mar. 5, 2024

(54) DOSAGE REGIMEN FOR INHALED VASOACTIVE INTESTINAL POLYPEPTIDE

(71) Applicant: CENTURION İLAÇ SANAYI VE TICARET ANONIM ŞIRKETI, Istanbul (TR)

(72) Inventors: Güniz Çakar, Istanbul (TR); Mustafa Ersin Erfa, Istanbul (TR)

(73) Assignee: CENTURION İLAÇ SANAYI VE TICARET ANONIM SIRKETI, Istanbul (TR)

(*) Notice: Subject to any disclaimer, the term of this patent is extended or adjusted under 35 U.S.C. 154(b) by 0 days.

(21) Appl. No.: 17/542,134

(22) Filed: Dec. 3, 2021

(65) Prior Publication Data

US 2022/0175889 A1    Jun. 9, 2022

Related U.S. Application Data

(60) Provisional application No. 63/121,541, filed on Dec. 4, 2020.

(51) Int. Cl.
    *A61K 38/22*    (2006.01)
    *A61K 9/00*    (2006.01)
    *A61P 11/00*    (2006.01)

(52) U.S. Cl.
    CPC ........ *A61K 38/2278* (2013.01); *A61K 9/0078* (2013.01); *A61P 11/00* (2018.01)

(58) Field of Classification Search
    CPC .......................... A61K 38/2278; A61P 11/00
    See application file for complete search history.

(56) References Cited

U.S. PATENT DOCUMENTS 9,566,399 B1 *  2/2017  Bono ................ A61M 15/0086

FOREIGN PATENT DOCUMENTS

WO    WO-2006094764 A1 *  9/2006  ......... A61K 38/2278

OTHER PUBLICATIONS

Strong C, "Aviptadil Not Linked to Improvement in COVID-19 Hypoxemic Respiratory Failure," Pulmonology Advisor, Jul. 21, 2023, pp. 1-5. (Year: 2023).*
ClinicalTrials.gov NCT04360096, first submitted Apr. 21, 2020, pp. 1-11. (Year: 2020).*

* cited by examiner

*Primary Examiner* — Julie Ha
(74) *Attorney, Agent, or Firm* — Casimir Jones SC; Lisa Mueller

(57) ABSTRACT

Improved and effective administration regimen of aviptadil in order to reduce and eliminate the risks of nebulization treatment and to protect both patient relatives and healthcare workers especially in pandemic conditions such as Covid-19 is described. The dosage frequency of aviptadil for use in the treatment of lung diseases in a subject in need by thereof is administered at least 2 times in a day and the period between the administrations does not exceed 200 minutes.

18 Claims, No Drawings

DOSAGE REGIMEN FOR INHALED VASOACTIVE INTESTINAL POLYPEPTIDE

CROSS-REFERENCE TO RELATED APPLICATION

This application claims priority to U.S. Provisional Application No. 63/121,541, filed on Dec. 4, 2020, which is hereby incorporated by reference in its entirety.

TECHNICAL FIELD

The present invention relates to new dosage regimen of aviptadil for use in the treatment of lung diseases.

BACKGROUND ART

Since VIP agonists have potent bronchodilator and immunomodulatory effects in the respiratory system, their use has been suggested for asthma, pulmonary hypertension, chronic obstructive pulmonary disease, sarcoidosis, and COVID-19, as well as inflammatory upper respiratory tract diseases.

Inhaled VIP agonists show localized effects. Therefore, systemic side effects are expected to be less. (Mathioudakis, Chatzimavridou-Grigoriadou et al. 2013). Different inhalation dosages were evaluated. A single 375 µg inhaled VIP was briefly evaluated for protection against histamine-induced bronchoconstriction. Although the effectiveness of inhaled VIP was known, the activity could not be shown in this study. This lack of effectiveness of aerosolized VIP were explained by rapid metabolic inactivation or from avid binding to mucus layer proteins. Therefore no side effects were reported (Altiere, Kung et al. 1984). In another study, subjects received 100 µg VIP agonists as a single dose for determining the effect of inhaled VIP agonists on bronchial reactivity to histamine in humans (Barnes and Dixon 1984). For determination of the effect of VIP agonists on propranolol-induced bronchoconstriction, VIP was used as a single 70 µg dose inhalation in clinical tests (Crimi, Palermo et al. 1988).

In WO2003061680A2, inhaled VIP dose was described as between 5 µg, and 200 µg/kg body weight, preferably between 20 µg and 20 µg/kg body weight, and 100 µg and 200 ng doses were used in patients, but posology details were not described for this application. In US20060241028A1, VIP inhalation was used as four divided doses of 200 ng in 12 ml 0.9% NaCl per day for 12 weeks to treat sarcoidosis.

Endogenous Aviptadil is a 28 amino acid neuropeptide/neurotransmitter, known as the vasoactive intestinal peptide (VIP) (Delgado and Ganea 2013). Aviptadil is a peptide that has been used in the United States and European countries for a long time.

There are prior arts describing studies with aviptadil. For example, EP 1 855 661 B1 discloses controlled experiments carried out on humans and animals. Herein, the daily dose used in the experiments is 400 micrograms split in 4 single doses of 100 micrograms of aviptadil each. The effect of aviptadil on patients suffering from pulmonary hypertension associated to post-ventricular septal defect (post-VSD), associated to CREST Syndrome, associated to extrinsic allergic alveolitis, associated to COPD and idiopathic pulmonary arterial hypertension (IPAH) are investigated.

In addition, for primary pulmonary hypertension treatment with 4 single inhalations of a total of 200 µg Aviptadil per day was investigated by Petkov et. al. They defined a new concept for the treatment of primary pulmonary hypertension with a vasoactive intestinal peptide due to its potent systemic and pulmonary vasodilator effect: a concentration range of 100-200 µg per day that is predicted to be effective and 200 µg per day was tested (Petkov, Mosgoeller et al. 2003). A single 100 µg dose of inhaled Aviptadil was also used to treat pulmonary hypertension (Leuchte, Baezner et al. 2008). Herein, for testing the acute effects on hemodynamics and blood gases, and the safety of a single dose of inhaled Aviptadil in chronic pulmonary hypertension (PH), a total of 20 patients with PH inhaled a single 100-µg dose of Aviptadil during right-heart catheterization. In another study, an open clinical phase II study was planned to test whether inhaled VIP has an immunomodulatory role. Twenty patients with histologically proven sarcoidosis and active disease were treated with nebulized VIP for 4 weeks. The patients received 50 µg synthetic VIP four times daily by inhalation with an ultrasonic nebulizer for 28 days to evaluate the immunoregulatory effects of VIP in sarcoidosis (Prasse, Zissel et al. 2010). Inhaled formulation of Aviptadil, was used at a dose of 70 µg three times daily as a local therapy to reduce the alveolar inflammation found in patients with immune checkpoint inhibitor pneumonitis (Frye, Meiss et al. 2020). Barnes et.al. studied the effect of VIP on bronchomotor tone and bronchial response to inhaled histamine. They gave 6 atopic asthmatic subjects VIP (100 µg) and control solution double-blind in random order on separate days and compared their effects (Barnes and Dixon 1984). In a study with asthmatic patients β-adrenergic- and cholinergic-receptor blockage was achieved and the effect of inhaled VIP (70 µg) on bronchomotor tone was evaluated. The study was performed in six patients with asthma in 4 days (Crimi, Palermo et al. 1988). Thus, aviptadil's administration method, especially for nebulizer formulations, is investigated for many years.

Nebulizers can generate 1-5 µm aerosol particles that can carry bacteria and viruses deep into the lungs. The risk of infection transmission through droplet nuclei and aerosols may increase in treatments with nebulizers. The spread of a virus is a complex event and requires an inoculum, a sufficient amount of pathogen, and a host. Transmission routes for respiratory viruses can be listed as follows: contact (skin to skin or object/surface), by droplets, or by aerosol transmission. Droplets, which can occur with coughing and sneezing, are more extensive than aerosols (greater than 5-10 µm). Since they are large particles, they cannot spread beyond 1 m, but they can cause contamination by contact by adhering to a surface. On the other hand, aerosols occur during breathing and stay in the air for a long time (Sethi, Barjaktarevic et al. 2020)

There is a risk of transmission due to the respiratory aerosols in nebulizer treatments (Amirav and Newhouse 2020). As it is known, nebulization causes the particles to disperse in the environment (Reychler, Vecellio et al. 2020). These aerosol particles are thought to be able to travel long distances.

Nebulizer therapy in patients with COVID-19 infection has the potential to transmit the viable coronavirus to susceptible hosts in their environment. (Amirav and Newhouse 2020). Considering that the currently planned clinical trials requires the patients to use the nebulizers three times a day, the risk of transmission of the pathogens would be high. It can be considered as a possibility that C OVID-19 patients who receive nebulizer therapy may cause the virus to spread (Amirav and Newhouse 2020). In other words, healthcare workers and the patients would be at the risk for a serious infection not only for Covid-19 but also for other infectious diseases for a long period of time.

Although studies on the relationship between nebulization and the spread of COVID-19 are ongoing, some findings suggest that nebulization treatments are associated with the spread of C OVID-19. Aerosol generating therapies, including nebulization, were administered to one patient in California. During this treatment period, 43 of the 121 healthcare workers who did not use protective equipment when confronted with the patient showed symptoms of COVID-19, while 3 were positive. However, the relationship between nebulization and COVID-19 has not been demonstrated (Heinzerling, Stuckey et al. 2020) In another study, a live attenuated influenza vaccine as a surrogate virus tracer was used. According to the survey, the breathing of an adult patient undergoing nebulization treatment with a jet nebulizer and face mask was simulated, and air samples collected from 3 different points were examined. While 612 viruses were detected per liter in the sample taken from the area near the head of the patient, 174 viruses per liter were detected in the area near the abdomen. 118 viruses/liter was detected in the area around the foot of the patient. This study revealed that aerosols' emission concentrations decrease with distance from the patient (Tang, Kalliomaki et al. 2020). The risk of virus transmission may increase since viral secretions can enter the reservoir of the jet nebulizer used with a face mask (McGrath, O'Toole et al. 2019). It has been suggested that nebulizers be used with a mouthpiece to prevent spreading (Sethi, Barjaktarevic et al. 2020).

Société de Pneumologie de Langue Franc's Aerosol-therapy (GAT) working group recommended avoiding drug delivery by nebulization during the SARS-CoV-2 outbreak. Thus, it is aimed to prevent the spread of the virus by nebulization. Nebulizers can infect patients with various microbes, as shown in many studies. These studies can also be extrapolated for SARS-CoV-2, and nebulizers may be thought to be infectious (Reychler, Vecellio et al. 2020). It has also been shown that SARS-CoV-2 can survive on plastic for 72 hours (van Doremalen, Bushmaker et al. 2020). Thus, particles produced by contaminated nebulizers during the nebulization session will spread from the patient to the people around the patient or even to healthcare workers. The nebulizer reservoir is not fully protected during nebulization treatments. Reservoirs may be contaminated by patients' hands or patient saliva. Thus, it can penetrate the upper and lower respiratory tract of healthcare workers by traveling long distances, as it has the appropriate particle size (Reychler, Vecellio et al. 2020).

An in vitro study was conducted to examine the stability of the virus in aerosols. In this study, an aerosol jet nebulizer containing SARS-CoV-2 was prepared, and it was determined that the virus remained alive for 3 hours in aerosols after nebulization. Similar results were obtained when the experiment was repeated with SARS-CoV-1 (van Doremalen, Bushmaker et al. 2020). Since SARS-CoV-1 is suggested to be airborne, SARS-CoV-2 may also be airborne.

Studies are ongoing on the transport of COVID-19 by post-nebulization aerosol droplets in patients treated with nebulization, but there is not enough evidence yet. The Canadian Pediatric Society and the Global Initiative for Asthma have recommended that nebulizers not be used unless necessary. Besides, The National Institute for Health and Care Excellence (NICE) and Public Health England (PHE) recommends that nebulization therapy be continued when feasible. The Centers of Disease Control and Prevention (CDC) also did not oppose treatment with nebulization but said it was in the unknown exposure category for healthcare workers (Sethi, Barjaktarevic et al. 2020).

Based on the information provided, the inventors consider it would be reasonable to limit the usage of nebulization only in necessary patients, and for fewer times in a day, to reduce the risk of exposure to healthcare workers (Reychler, Vecellio et al. 2020). In addition, there are prior arts disclosing the use of aviptadil in the treatment of Covid-19. In recent clinical trials, 100 µg inhaled Aviptadil will be used three times a day (NCT04360096) for treatment of COVID-19 with a mesh nebulizer. In another study (NCT04536350), participants will receive standard care plus a dose of 67 µg nebulized Aviptadil three times a day for ten days for the prevention of COVID-19 related ARDS.

However, as explained before, COVID-19 patients who must use the nebulization treatment method are a risk factor for both their environment and healthcare professionals. There is still a need for improved and effective administration regimen of aviptadil in order to reduce and eliminate the risks of nebulization treatment.

DETAILED DESCRIPTION OF THE INVENTION

The present invention provides a method of treating a lung disease in a subject in need thereof by administering of an effective dose of aviptadil to the subject.

In one embodiment, the present invention provides aviptadil for use in the treatment of a lung disease in a subject in need thereof wherein said composition is administered at least 2 times in a day, preferably 2 times in a day compared to the prior art administration regimes. Thus, the virus transmission is decreased by reducing the dosing frequency instead of giving aviptadil by nebulization 3 times a day. The inventors aim to protect both patient relatives and healthcare workers especially in pandemic conditions such as Covid-19.

According to the present invention, aviptadil for use in the treatment of a lung disease in a subject in need thereof is administered at least 2 times in a day, preferably 2 times in a day, wherein the period between the administrations does not exceed 200 minutes or preferably the period between the administrations is from 5 to 120 minutes; more preferably from 15 to 110 minutes, from 20 to 100 minutes, from 25 to 90 minutes or from 15 to 90 minutes and most preferably 30 minutes. It has been surprisingly found that by significantly reducing the period between the administrations of aviptadil it is possible to provide a treatment while reducing the spread of virus and to increase the patient compliance without any side effects.

In another embodiment of the present invention, aviptadil is administered three times in a day wherein the period between the administrations does not exceed 200 minutes or preferably the period between the administrations is from 5 to 120 minutes; more preferably from 15 to 90 minutes and most preferably 30 minutes.

In all embodiment of the present invention, the treatment is continued for between 3 to 30 days, preferably between 5 to 21 days and more preferably between 7 to 14 days.

Herein, the term "dose" is the amount of aviptadil that is to be administered at one time. The dose of aviptadil is between 1 to 150 µg, preferably between 40 to 120 µg and more preferably 100 µg.

According to the present invention, aviptadil is administered at least 2 times in a day. Thus, the administration comprises a first and second doses. The first dose of aviptadil is between 1 to 150 µg, preferably between 40 to 120 µg and more preferably 100 µg. The second dose of aviptadil is between 1 to 150 µg, preferably between 40 to 120 µg and more preferably 100 µg.

According to the present invention, aviptadil is used for the treatment of a lung disease; preferably Covid-19 disease caused by SARS-CoV-2 virus, asthma, pulmonary hypertension, chronic obstructive pulmonary disease, sarcoidosis or berylliosis; and more preferably Covid-19 disease caused by SARS-CoV-2 virus.

According to the present invention, the administration of aviptadil is applied with a nebulizer, preferably M-neb mobile mesh nebulizer MN-300/9.

In all embodiments, the present invention provides a pharmaceutical composition of aviptadil for pulmonary administration for use in the treatment of lung disease. The composition is suitable for being delivered by a nebulizer.

According to the present invention, the composition comprises aviptadil in the range of 0.001-1% w/v.

In one embodiment of the present invention, the composition of aviptadil comprises at least one additional excipient which may be preservatives, antioxidants, chelating agents, buffering agents, acidifying agents, emulsifiers, alkalizing agents, coloring agents, solubilizers, stabilizers, plasticizers, viscosity modifiers or other excipients which are known in the prior art.

The composition of the present invention may comprise at least one emulsifier which may be selected from the group consisting of polysorbates, lecithins, alginic acid, alginates, gums, salts of fatty acids, microcrystalline cellulose, methylcellulose, hydroxypropylcellulose, hydroxypropylmethylcellulose, ethylmethylcellulose, carboxymethylcellulose or combinations thereof.

The composition of the present invention may also comprise at least one chelating agent which may be selected from the group consisting of EDTA or one of the known salts thereof (tetrasodium EDTA, disodium EDTA or sodium EDTA), sodium metasilicate, DTPA, NT or combinations thereof.

The composition of the present invention may also comprise at least one buffering agent which may be selected from the group consisting of sodium citrate, citric acid, trisodium citrate, a carbonate buffer, a hydroxide buffer, a phosphate buffer and an acetate buffer or combinations thereof.

According to the present invention, the composition is a dispersion of particles of aviptadil having a mass median aerodynamic diameter (MMAD) between 1 and 5 µm.

In a preferred embodiment of the present invention, aviptadil for use in the treatment of the lung disease is in a salt form, preferably acetate salt.

The composition according to the present invention may be obtained by a process comprising the steps of mixing aviptadil with the excipients and of adjusting the pH of composition. The process also comprises the steps of filtration and filling. In the process, the excipients are solved in water and then aviptadil is added to the composition of excipients and solved. The pH is adjusted to 5.7. Sterile filtration and filling steps are executed.

EXAMPLES

Example 1

In the study, placebo and treatment groups were compared. In placebo group, standard medical treatment, as deemed appropriate by physicians, is going to be according to the Turkish Republic COVID-19 (SARS-CoV-2 INFECTION) ADULT PATIENT TREATMENT GUIDELINES published by the Ministry of Health, General Directorate of Public Health and placebo will be used.

Current formulation of Investigational Medicinal Product and Placebo were listed below (Table 1). Both of Investigational Medicinal Product and Placebo were manufactured as sterile and compatible with good manufacturing requirements.

TABLE 1

Contents of Investigational Medicinal Product and Placebo

|  | Investigational Medicinal Product (mg/vial) | Placebo(mg/vial) |
| --- | --- | --- |
| Aviptadil* | 0.100 | — |
| Sodium chloride | 8.50 | 8.50 |
| Trisodium citrate | 0.50 | 0.50 |
| Polysorbate 80 | 0.20 | 0.20 |
| Disodium EDTA | 0.46 | 0.46 |
| Citric acid | q.s. | q.s. |
| Water | 1 ml | 1 ml |

*added as acetate salt

In the treatment group, in addition to the standard medical treatment mentioned above, patients randomized to this arm will be given inhaled Aviptadil 2 times in a day wherein the period of administration between both doses is 30 minutes. M-neb mobile mesh nebulizer MN-300/9 was used for nebulization. Mass Median Aerodynamic Diameter is 4±0.16 µm. Aviptadil treatment is aimed to be a minimum of 7 days and a maximum of 14 days. The study population will consist of patients 18 years of age and older with COVID-19 pulmonary involvement and hospitalized patients. The Efficacy, Safety and Tolerability of Inhaled Aviptadil with New Posology were evaluated. The rate of patients entering intensive care was evaluated as efficacy parameter.

Results:

Our main target is developing a new dosage regimen for Aviptadil for use in Covid-19 patients with reduced risk of transmission of COVID-19 infection without side effects. 16 patients were enrolled in treatment group and 13 patients enrolled in placebo group. In this method, new dosage of inhaled Aviptadil is well tolerated by patients. 47 adverse events are observed in 27 patient and 40.43% percent of these adverse events observed in Treatment Group. None of adverse events was found related with Investigational Medicinal Product (Table 2).

TABLE 2

Adverse Event Distribution

|  | Adverse Events (AEs) Related with Investigational Medicinal Product |
| --- | --- |
| No | 47 |
| Yes | 0 |
|  | Distribution of AEs (%) |
| Treatment | 40.43 |
| Placebo | 59.57 |

When the rate of patients entering intensive care was evaluated in treatment group in 60 years and older patients, it was observed that percent of entering intensive care was found 25% in treatment group and 66.7% in placebo group (Table 3).

TABLE 3

Age Related Distribution of Entering Intensive Care
Entering Intensive Care (%)

|  | Age >= 60 |
|---|---|
| Treatment | 25.0% |
| Placebo | 66.7% |

Conclusion

The present invention provides a new dosage regimen for Aviptadil for use in Covid-19 patients with reduced risk of transmission of COVID-19 infection without side effects. By this aim, performed study demonstrated that Investigational Medicinal Product was well tolerated by all patients and effective in the high-risk age group. No drug and posology related adverse event were observed in this dose regimen.

The invention claimed is:

1. A method of treating a coronavirus disease 2019 (COVID-19) and complications of the disease caused by a severe acute respiratory syndrome (SARS) CoV-2 virus in a patient in need thereof comprising administering to the patient aviptadil at least 2 times in a day, wherein the period between administration is between 5 to 200 minutes, and wherein the aviptadil is administered with a nebulizer.

2. The method according to claim 1, wherein aviptadil is administered 2 times in a day.

3. The method according to claim 1, wherein the first dose of aviptadil is between 1 to 150 µg.

4. The method according to claim 1, wherein the first dose of aviptadil is between 40 to 120 µg.

5. The method according to claim 1, wherein the first dose of aviptadil is 100 µg.

6. The method according to claim 1, wherein the second dose of aviptadil is between 1 to 150 µg.

7. The method according to claim 1, wherein the second dose of aviptadil is between 40 to 120 µg.

8. The method according to claim 1, wherein the second dose of aviptadil is 100 µg.

9. The method according to claim 1, wherein the period between administrations is between 15 to 120 minutes.

10. The method according to claim 1, wherein the treatment is continued for 5 to 21 days.

11. The method according to claim 1, wherein the patient is at the age of 60 or older and is hospitalized with complications of COVID-19.

12. The method of claim 1, wherein the period between administration is between 15 to 30 minutes.

13. The method of claim 1, wherein period between administration is 30 minutes.

14. The method of claim 13, wherein the first does of aviptadil is 100 µg, the second dose of aviptadil is 100 µg and the treatment is continued for at least 5 days.

15. The method of claim 13, wherein the first dose of aviptadil is 100 µg, the second dose of aviptadil is 100 µg and the treatment is continued for 7 days.

16. The method of claim 1, wherein:
the first dose of aviptadil is 100 µg;
the second dose of aviptadil is 100 µg;
the period between administration is 30 minutes; and
the treatment is continued for 7 days.

17. The method according to claim 1, wherein the complications of the disease are respiratory complications.

18. The method according to claim 1, wherein the complications of the disease are selected from the group consisting of pneumonia, cough, dyspnea or trouble breathing, acute respiratory distress syndrome (ARDS), lung failure, impaired respiratory physiology, vascular complications, and pulmonary fibrosis.

* * * * *

UNITED STATES PATENT AND TRADEMARK OFFICE
CERTIFICATE OF CORRECTION

PATENT NO. : 11,918,627 B2
APPLICATION NO. : 17/542134
DATED : March 5, 2024
INVENTOR(S) : Güniz Çakar and Mustafa Ersin Erfa It is certified that error appears in the above-identified patent and that said Letters Patent is hereby corrected as shown below:

In the Claims

Claim 1, Column 7, Line 24 reads:
"between administration is between 5 to 200 minutes, and;"
Whereas it should read:
-- between administrations is between 5 to 200 minutes, and; --

Claim 12, Column 8, Line 13 reads:
"administration is between 15 to 30 minutes"
Whereas it should read:
-- administrations is between 15 to 30 minutes; --

Claim 13, Column 8, Line 15 reads:
"administration is 30 minutes"
Whereas it should read:
-- administrations is 30 minutes; --

Signed and Sealed this
Twenty-fifth Day of June, 2024

Katherine Kelly Vidal
*Director of the United States Patent and Trademark Office*